US00PP29849P2

(12) United States Plant Patent
Lannes

(10) Patent No.: US PP29,849 P2
(45) Date of Patent: Nov. 20, 2018

(54) ***MANDEVILLA* PLANT NAMED 'LANKENTUCKY'**

(50) Latin Name: *Mandevilla x amabilis X Mandevilla hybrida*
Varietal Denomination: Lankentucky

(71) Applicant: Robert Lannes, Malause (FR)

(72) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 15/731,678

(22) Filed: Jul. 15, 2017

(51) Int. Cl.
*A01H 5/02* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. A. Whealy

(57) ABSTRACT

A new and distinct cultivar of *Mandevilla* plant named 'Lankentucky', characterized by its compact, upright and twining plant habit; moderately vigorous growth habit; relatively thick stems, leaves and flower petals; glossy dark green-colored leaves; freely flowering habit; and bright red purple-colored flowers.

2 Drawing Sheets

Botanical designation: *Mandevilla* x *amabilis* X *Mandevilla hybrida.*

Cultivar denomination: 'LANKENTUCKY'.

BACKGROUND OF THE INVENTION

The present invention relates to a new and distinct cultivar of *Mandevilla* plant, botanically known as *Mandevilla* x *amabilis* X *Mandevilla hybrida* and hereinafter referred to by the name 'Lankentucky'.

The new *Mandevilla* plant is a product of a planned breeding program conducted by the Inventor in Malause, France. The objective of the breeding program is to create new *Mandevilla* plants with good plant habit and numerous attractive flowers.

The new *Mandevilla* plant originated from a cross-pollination conducted by the Inventor in Malause, France in June, 2015 of a proprietary selection of *Mandevilla* x *amabilis* identified as code number SI 08831-189, not patented, as the female, or seed, parent with *Mandevilla hybrida* 'Lansouthcarolina', disclosed in U.S. Plant Pat. No. 26,406, as the male, or pollen, parent. The new *Mandevilla* plant was discovered and selected by the Inventor as a single flowering plant from within the progeny of the stated cross-pollination in a controlled greenhouse environment in Malause, France in July, 2016.

Asexual reproduction of the new *Mandevilla* plant by cuttings in a controlled greenhouse environment in Malause, France, since September, 2016 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lankentucky'. These characteristics in combination distinguish 'Lankentucky' as a new and distinct *Mandevilla* plant:

1. Compact, upright and twining plant habit.
2. Moderately vigorous growth habit.
3. Relatively thick stems, leaves and flower petals.
4. Glossy dark green-colored leaves.
5. Freely flowering habit.
6. Bright red purple-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* are more compact and have shorter internodes than plants of the female parent selection.
2. Plants of the new *Mandevilla* are more freely flowering and flower more continuously than plants of the female parent selection.

Plants of the new *Mandevilla* can be compared to plants of the male parent, 'Lansouthcarolina'. Plants of the new *Mandevilla* differ primarily from plants of 'Lansouthcarolina' in the following characteristics:

1. Leaves of plants of the new *Mandevilla* are glabrous whereas leaves of plants of 'Lansouthcarolina' are densely pubescent.
2. Petals of plants of the new *Mandevilla* are broader and more rounded than petals of plants of 'Lansouthcarolina'.
3. Plants of the new *Mandevilla* and 'Lansouthcarolina' differ in flower color as plants of 'Lansouthcarolina' have pink-colored flowers.

Plants of the new *Mandevilla* can also be compared to plants of *Mandevilla sanderi* 'Fisrix Hopink', disclosed in U.S. Plant Pat. No. 20,672. In side-by-side comparisons, plants of the new *Mandevilla* differ primarily from plants 'Fisrix Hopink' in the following characteristics:

1. Plants of the new *Mandevilla* are more upright than and not as spreading as plants of 'Fisrix Hopink'.
2. Plants of the new *Mandevilla* have thicker leaves and petals than plants of 'Fisrix Hopink'.
3. Plants of the new *Mandevilla* are more freely flowering than plants of 'Fisrix Hopink'.
4. Plants of the new *Mandevilla* and 'Fisrix Hopink' differ in flower color as plants of 'Fisrix Hopink' have rose red to cherry red-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lankentucky' grown in a container.

The photograph on the second sheet is a close-up view of a typical open flower and flower bud of 'Lankentucky'.

DETAILED BOTANICAL DESCRIPTION

The aforementioned photographs and following observations, measurements and values describe plants grown during the late spring and early summer in 17-cm containers in polyethylene-covered greenhouse in Malause, France and under cultural practices typical of commercial *Mandevilla* production. During the production of the plants, day temperatures ranged from 15° C. to 26° C. and night temperatures ranged from 14° C. to 15° C. Plants were nine months old when the photographs and description were taken. In the following description, color references are made to The Royal Horticultural Society Colour Chart, 2015 Edition, except where general terms of ordinary dictionary significance are used.

Botanical classification: *Mandevilla* x *amabilis* X *Mandevilla hybrida* 'Lankentucky'.

Parentage:

*Female, or seed, parent*.—Proprietary selection of *Mandevilla* x *amabilis* identified as code number SI 08831-189, not patented.

*Male, or pollen, parent*.—*Mandevilla hybrida* 'Lansouthcarolina', disclosed in U.S. Plant Pat. No. 26,406.

Propagation:

*Type*.—By vegetative cuttings.

*Time to initiate roots, summer*.—About four weeks at temperatures about 18° C. to 30° C.

*Time to initiate roots, winter*.—About five weeks at temperatures about 16° C. to 25° C.

*Time to produce a rooted young plant, summer*.—About ten weeks at temperatures about 18° C. to 30° C.

*Time to produce a rooted young plant, winter*.—About twelve weeks at temperatures about 16° C. to 25° C.

*Root description*.—Fibrous, fine; typically light yellowish white in color, actual color of the roots is dependent on substrate composition, water quality, fertilizers, substrate temperature and physiological age of roots.

*Rooting habit*.—Freely branching; medium density.

Plant description:

*Plant and growth habit*.—Compact, upright and twining plant habit; overall plant shape is broadly oblong; moderately vigorous growth habit.

*Plant height, soil level to top of foliar plane*.—About 43.5 cm.

*Plant height, soil level to top of floral plane*.—About 48.8 cm.

*Plant diameter* (*spread*).—About 31.9 cm.

*Lateral branch description*.—Branching habit: Freely branching habit with about six primary lateral branches, each with about twelve secondary lateral branches developing per plant. Length: About 26.4 cm. Diameter: About 3.5 mm. Internode length: About 5.8 cm. Strength: Strong. Texture and luster: Smooth, glabrous; glossy. Color, developing: Close to 144A. Color, developed: Close to 199A and 199B.

Leaf description:

*Arrangement*.—Opposite, simple.

*Length*.—About 9.3 cm.

*Width*.—About 6.1 cm.

*Shape*.—Ovate to obovate and oblong.

*Apex*.—Short apiculate.

*Base*.—Obtuse to truncate.

*Margin*.—Entire; coarsely undulate.

*Texture and luster, upper surface*.—Smooth, glabrous; glossy.

*Texture and luster, lower surface*.—Smooth, glabrous; slightly glossy.

*Venation pattern*.—Pinnate.

*Color*.—Developing leaves, upper surface: Slightly darker than 143A. Developing leaves, lower surface: Close to between 144A and 146B. Full expanded leaves, upper surface: Darker than between NN137A and 147A; venation, close to 144A. Fully expanded leaves, lower surface: Close to 147B; venation, close to 144B.

*Petioles*.—Length: About 7 mm. Diameter: About 3 mm by 4 mm. Strength: Moderately strong. Texture and luster, upper and lower surfaces: Smooth, glabrous; glossy. Color, upper surface: Close to 144A to 144B. Color, lower surface: Close to 145B.

Flower description:

*Flower type and flowering habit*.—Single salverform flowers arranged in axillary cymes; flowers star-shaped and face mostly upright and outwardly; freely flowering habit with about eight flowers developing per inflorescence and about 10 open flowers and about 90 flower buds develop per plant.

*Natural flowering season*.—Plants flower continuously from spring into the autumn in France.

*Flower longevity on the plant*.—About 15 days; flowers not persistent.

*Fragrance*.—Faint; sweet and pleasant.

*Inflorescence height*.—About 10.2 cm.

*Inflorescence diameter*.—About 13.2 cm.

*Flower buds*.—Length: About 5.6 cm. Diameter: About 1 cm. Shape: Narrowly oblanceolate. Texture and luster: Smooth, glabrous; slightly glossy. Color: Close to 49A and 49B; towards the base, close to 145B; stripes, close to 50C.

*Flowers*.—Appearance: Flared trumpet, corolla fused and five-parted. Diameter: About 8.2 cm. Depth (length): About 8.3 cm. Throat diameter: About 1.6 cm. Tube length: About 5.1 cm. Tube diameter, mid-section: Close to 5 mm.

*Corolla*.—Quantity and arrangement: Five petals arranged in a single whorl and fused towards the base forming a funnel-shaped tube. Petal length: About 8.9 cm. Petal width: About 4.3 cm. Petal shape and appearance: Roughly spatulate; lower 60% of the petal is fused into a tube. Petal apex: Acute to rounded. Petal margin: Entire; slightly undulate. Petal texture and luster, upper surface: Smooth, glabrous; moderately velvety; matte. Petal texture and luster, lower surface: Smooth, glabrous; glossy. Throat texture: Smooth, glabrous; moderately velvety. Tube texture: Smooth, glabrous; slightly velvety. Color: Petal, when opening, upper surface: Close to N57B and N57C. Petal, when opening, lower surface: Close to 67D and 62B. Petal, fully opened, upper surface: Close to 58B; venation, close to 58B; color does not change with development. Petal, fully opened, lower surface: Close to between 61D and 58C; venation, close to between 61D and 58C; color does not change with development. Throat: Close to 50B; venation, close to 50B. Tube: Close to 145B; venation, close to 145B.

*Corona*.—Quantity and arrangement: Five sepals arranged in a single whorl. Calyx length: About 7 mm. Calyx diameter: About 5 mm. Sepal length: About 7 mm. Sepal width: About 1 mm. Sepal shape: Narrowly deltoid. Sepal apex: Narrowly acute. Sepal base: Broadly cuneate. Sepal margin: Entire. Sepal texture and luster, upper surface: Smooth, glabrous; glossy. Sepal texture and luster, lower surface: Smooth, glabrous; matte. Sepal color: When opening, upper and lower surfaces: Close to 145B. Fully opened, upper surface: Close to 145A to 145B. Fully opened, lower surface: Close to 145A.

*Peduncles*.—Length: About 8.1 cm. Diameter: About 3 mm. Strength: Strong. Aspect: About 25° from vertical. Texture and luster: Smooth, glabrous; glossy. Color: Close to 144A.

*Pedicels*.—Length: About 1.7 cm. Diameter: About 3 mm. Strength: Strong. Aspect: About 40° from peduncle axis. Texture and luster: Smooth, glabrous; glossy. Color: Close to 144C.

*Reproductive organs*.—Stamens: Quantity and arrangement: Typically five; basifixed; anthers connivent. Filament length: About 1 mm. Filament color: Close to 153C. Anther shape: Narrowly oblong. Anther length: About 7 mm. Anther diameter: About 1.25 mm. Anther color: Close to 160B. Pollen amount: None observed. Pistils: Quantity: Typically one. Pistil length: About 2.1 cm. Style length: About 1.85 cm. Style color: Close to 145C. Stigma diameter: About 1.5 mm. Stigma shape: Club-shaped. Stigma color: Close to 146C. Ovary color: Close to 144A.

*Seeds and fruits*.—Seed and fruit production have not been observed on plants of the new *Mandevilla* to date.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be suitable for USDA Hardiness Zones 9 through 13.

It is claimed:

1. A new and distinct *Mandevilla* plant named 'Lankentucky' as illustrated and described.

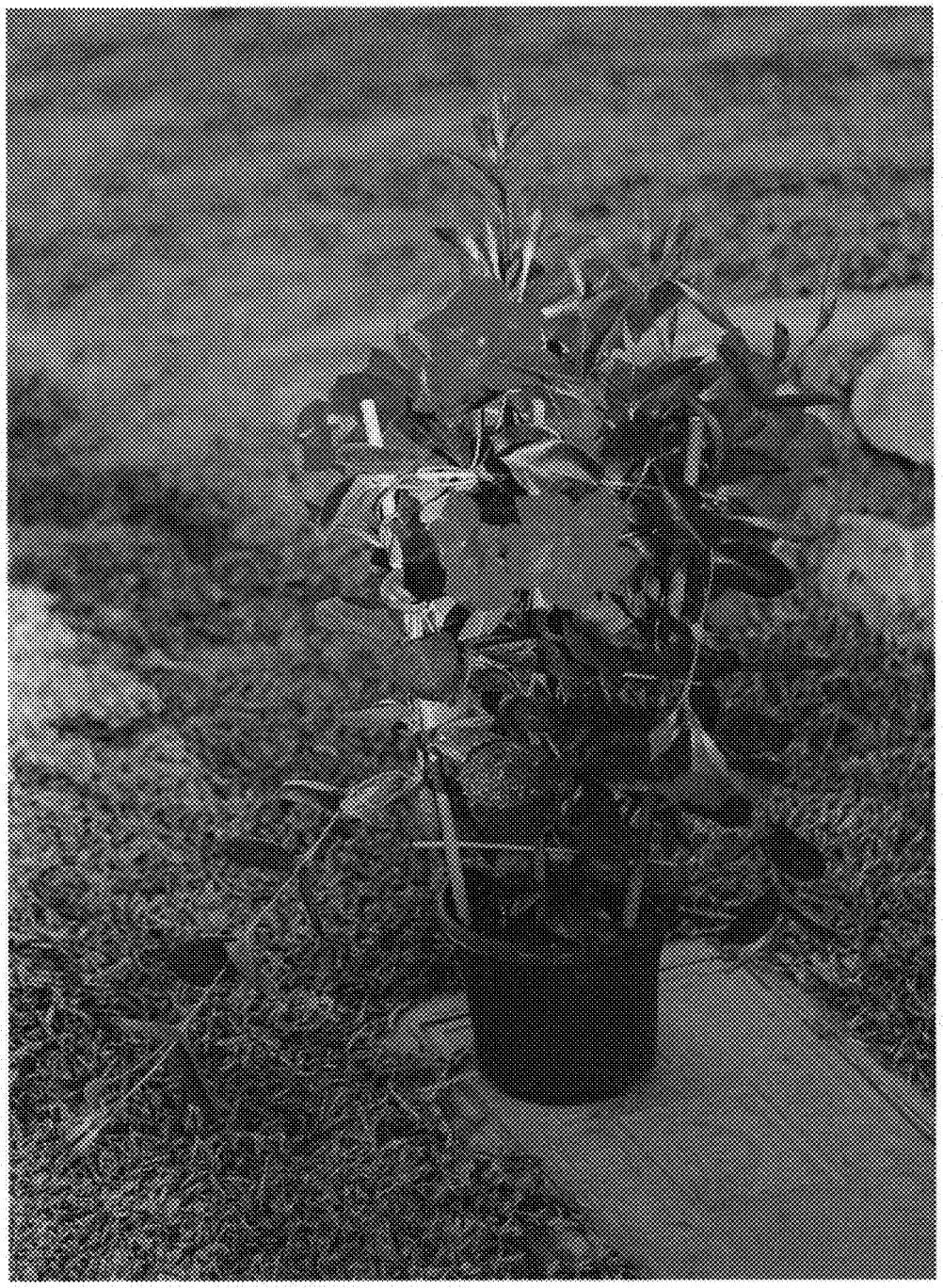

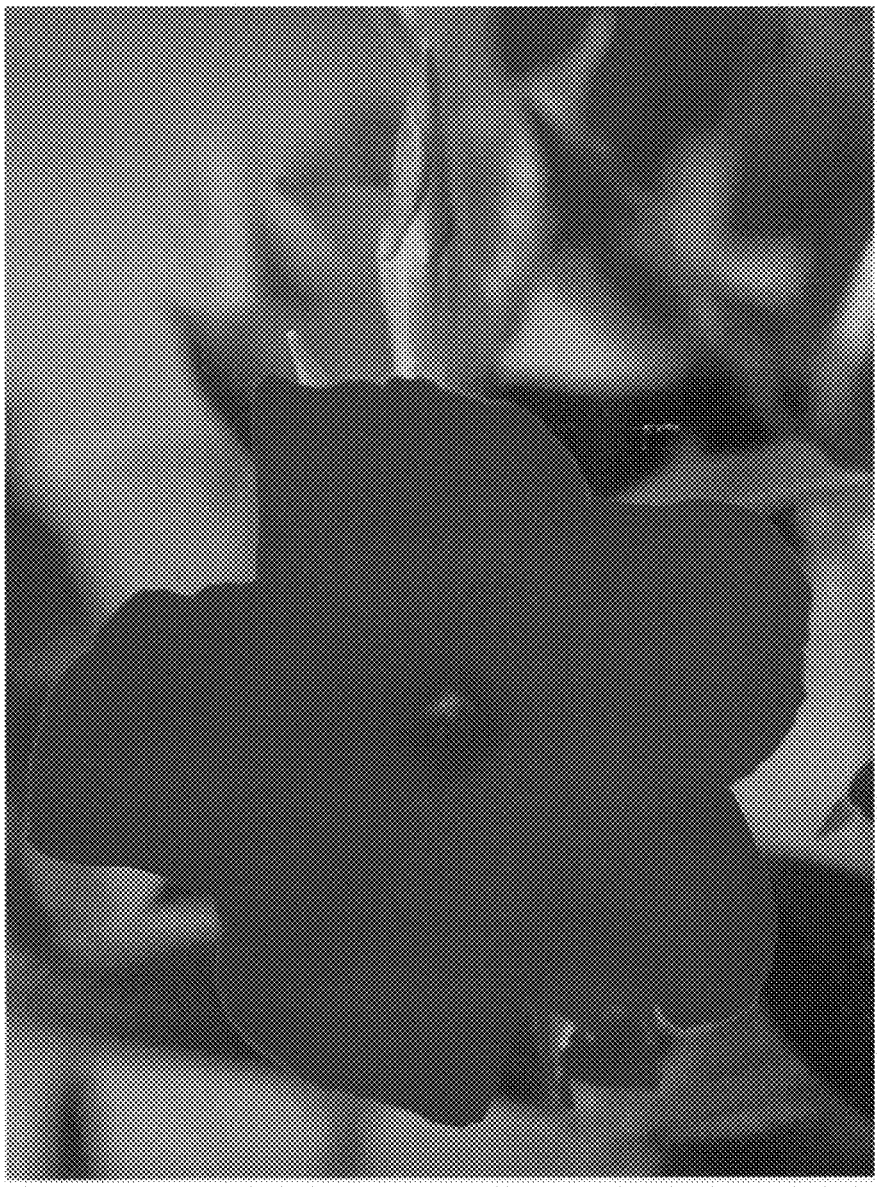

* * * * *